(12) United States Patent
Siemionow et al.

(10) Patent No.: US 11,278,359 B2
(45) Date of Patent: Mar. 22, 2022

(54) GRAPHICAL USER INTERFACE FOR USE IN A SURGICAL NAVIGATION SYSTEM WITH A ROBOT ARM

(71) Applicant: Holo Surgical Inc., Chicago, IL (US)

(72) Inventors: Krzysztof B. Siemionow, Chicago, IL (US); Cristian J. Luciano, Evergreen Park, IL (US); Edwing Isaac Mejia Orozco, Warsaw (PL)

(73) Assignee: Holo Surgical, Inc., Chicago, IL (US)

( * ) Notice: Subject to any disclaimer, the term of this patent is extended or adjusted under 35 U.S.C. 154(b) by 408 days.

(21) Appl. No.: 16/217,073

(22) Filed: Dec. 12, 2018

(65) Prior Publication Data
US 2019/0175285 A1 Jun. 13, 2019

(30) Foreign Application Priority Data
Dec. 12, 2017 (EP) .................................. 17206558

(51) Int. Cl.
*A61B 34/00* (2016.01)
*G02B 27/01* (2006.01)
(Continued)

(52) U.S. Cl.
CPC ............ *A61B 34/25* (2016.02); *A61B 5/7267* (2013.01); *A61B 34/10* (2016.02); *A61B 34/30* (2016.02);
(Continued)

(58) Field of Classification Search
CPC ......... A61B 34/25; A61B 34/30; A61B 34/10; A61B 34/20; A61B 90/36; A61B 90/37; A61B 5/7267; A61B 2090/3618; A61B 2090/368; A61B 2090/365; A61B 2090/3762; A61B 2090/363; A61B 2090/372; A61B 2090/3983; A61B 2090/367; A61B 2090/602;
(Continued)

(56) References Cited

U.S. PATENT DOCUMENTS 6,405,072 B1   6/2002   Cosman
8,314,815 B2   11/2012  Navab et al.
(Continued)

FOREIGN PATENT DOCUMENTS

CN   106600568 A    4/2017
EP   2 922 025 A1   9/2015
(Continued)

OTHER PUBLICATIONS

Non-Final Office Action dated Nov. 16, 2020 for U.S. Appl. No. 16/101,459, 43 pages.
(Continued)

*Primary Examiner* — Peter Luong

(57) ABSTRACT

A surgical navigation system includes: a tracker (125) for real-time tracking of a position and orientation of a robot arm (191); a source of a patient anatomical data (163) and a robot arm virtual image (166); a surgical navigation image generator (131) generating a surgical navigation image (142A) including the patient anatomy (163) and the robot arm virtual image (166) in accordance to the current position and/or orientation data provided by the tracker (125); a 3D display system (140) showing the surgical navigation image (142A).

20 Claims, 14 Drawing Sheets

(51) Int. Cl.
*G06T 19/00* (2011.01)
*G06F 3/01* (2006.01)
*A61B 34/10* (2016.01)
*A61B 90/00* (2016.01)
*G06T 7/11* (2017.01)
*A61B 5/00* (2006.01)
*G06T 5/00* (2006.01)
*A61B 34/30* (2016.01)
*A61B 34/20* (2016.01)
*A61B 90/50* (2016.01)
*A61B 17/00* (2006.01)
*G06K 9/62* (2022.01)
*G06T 7/20* (2017.01)

(52) U.S. Cl.
CPC .............. *A61B 90/36* (2016.02); *A61B 90/37* (2016.02); *G02B 27/017* (2013.01); *G02B 27/0172* (2013.01); *G06F 3/012* (2013.01); *G06F 3/013* (2013.01); *G06T 5/002* (2013.01); *G06T 7/11* (2017.01); *G06T 19/006* (2013.01); *A61B 34/20* (2016.02); *A61B 2017/00216* (2013.01); *A61B 2034/102* (2016.02); *A61B 2034/105* (2016.02); *A61B 2034/107* (2016.02); *A61B 2034/2055* (2016.02); *A61B 2034/2063* (2016.02); *A61B 2034/2068* (2016.02); *A61B 2090/363* (2016.02); *A61B 2090/365* (2016.02); *A61B 2090/367* (2016.02); *A61B 2090/368* (2016.02); *A61B 2090/3618* (2016.02); *A61B 2090/372* (2016.02); *A61B 2090/3762* (2016.02); *A61B 2090/3983* (2016.02); *A61B 2090/502* (2016.02); *G02B 2027/0134* (2013.01); *G02B 2027/0136* (2013.01); *G02B 2027/0138* (2013.01); *G02B 2027/0178* (2013.01); *G02B 2027/0187* (2013.01); *G02B 2027/0196* (2013.01); *G06K 9/6257* (2013.01); *G06K 2209/055* (2013.01); *G06T 7/20* (2013.01); *G06T 2207/10081* (2013.01); *G06T 2207/20081* (2013.01); *G06T 2207/20084* (2013.01); *G06T 2207/30012* (2013.01); *G06T 2207/30208* (2013.01); *G06T 2219/004* (2013.01)

(58) Field of Classification Search
CPC .. A61B 2017/00216; A61B 2034/2063; A61B 2034/105; A61B 2034/107; A61B 2034/102; A61B 2034/2055; A61B 2034/2068; G02B 27/017; G02B 27/0172; G02B 2027/0136; G02B 2027/0187; G02B 2027/0134; G02B 2027/0196; G02B 2027/0178; G06T 7/11; G06T 7/20; G06T 5/002; G06T 19/006; G06T 2207/10081; G06T 2207/20081; G06T 2207/20084; G06T 2207/30012; G06T 2207/30208; G06T 2219/004; G06F 3/012; G06F 3/013; G06K 9/6257; G06K 2209/055
See application file for complete search history.

(56) References Cited

U.S. PATENT DOCUMENTS

| | | | |
|---|---|---|---|
| 8,933,935 B2 | 1/2015 | Yang et al. | |
| 9,289,267 B2 | 3/2016 | Sauer et al. | |
| 9,532,848 B2 | 1/2017 | Amiot et al. | |
| 9,949,700 B2 | 4/2018 | Razzaque et al. | |
| 10,016,243 B2 | 7/2018 | Esterberg | |
| 10,080,623 B2 | 9/2018 | Saito | |
| 10,105,187 B2 | 10/2018 | Corndorf et al. | |
| 10,292,768 B2* | 5/2019 | Lang | A61F 2/389 |
| 10,646,283 B2 | 5/2020 | Johnson et al. | |
| 10,646,285 B2 | 5/2020 | Siemionow et al. | |
| 10,653,497 B2 | 5/2020 | Crawford et al. | |
| 10,788,672 B2 | 9/2020 | Yadav et al. | |
| 10,939,977 B2 | 3/2021 | Messinger et al. | |
| 10,951,872 B2 | 3/2021 | Casas | |
| 2002/0082498 A1 | 6/2002 | Wendt et al. | |
| 2004/0047044 A1 | 3/2004 | Dalton | |
| 2005/0190446 A1 | 9/2005 | Kuerz et al. | |
| 2005/0289472 A1 | 12/2005 | Morita et al. | |
| 2006/0176242 A1 | 8/2006 | Jaramaz et al. | |
| 2008/0144773 A1 | 6/2008 | Bar-Zohar et al. | |
| 2010/0328433 A1 | 12/2010 | Li | |
| 2011/0229005 A1 | 9/2011 | Harder et al. | |
| 2011/0311113 A1 | 12/2011 | Baumgart | |
| 2012/0314224 A1 | 12/2012 | Luellau | |
| 2013/0226190 A1 | 8/2013 | Mckinnon et al. | |
| 2015/0018622 A1 | 1/2015 | Tesar et al. | |
| 2015/0125033 A1 | 5/2015 | Murphy et al. | |
| 2015/0177598 A1 | 6/2015 | Mima et al. | |
| 2015/0264339 A1 | 9/2015 | Riedel | |
| 2016/0035139 A1 | 2/2016 | Fuchs et al. | |
| 2016/0176242 A1 | 6/2016 | Nakamata | |
| 2016/0187969 A1 | 6/2016 | Larsen et al. | |
| 2016/0191887 A1* | 6/2016 | Casas | G02B 27/0172 348/47 |
| 2016/0278875 A1 | 9/2016 | Crawford et al. | |
| 2016/0324580 A1 | 11/2016 | Esterberg | |
| 2016/0328630 A1 | 11/2016 | Han et al. | |
| 2017/0024903 A1 | 1/2017 | Razzaque | |
| 2017/0042631 A1 | 2/2017 | Doo et al. | |
| 2017/0056115 A1 | 3/2017 | Corndorf et al. | |
| 2017/0084036 A1 | 3/2017 | Pheiffer et al. | |
| 2017/0112575 A1 | 4/2017 | Li et al. | |
| 2017/0258526 A1 | 9/2017 | Lang | |
| 2017/0323062 A1 | 11/2017 | Djajadiningrat et al. | |
| 2017/0329402 A1 | 11/2017 | Riedel | |
| 2017/0360395 A1 | 12/2017 | Razzaque | |
| 2018/0012416 A1 | 1/2018 | Jones et al. | |
| 2018/0042681 A1 | 2/2018 | Jagga | |
| 2018/0078316 A1 | 3/2018 | Schaewe et al. | |
| 2018/0082480 A1 | 3/2018 | White et al. | |
| 2018/0140362 A1 | 5/2018 | Cali et al. | |
| 2018/0174311 A1* | 6/2018 | Kluckner | G06K 9/6259 |
| 2018/0185113 A1 | 7/2018 | Gregorson et al. | |
| 2018/0225993 A1 | 8/2018 | Buras et al. | |
| 2018/0271484 A1 | 9/2018 | Whisler | |
| 2018/0303558 A1 | 10/2018 | Thomas | |
| 2018/0311012 A1* | 11/2018 | Moctezuma | A61B 34/25 |
| 2019/0029757 A1 | 1/2019 | Roh et al. | |
| 2019/0053851 A1 | 2/2019 | Siemionow et al. | |
| 2019/0105009 A1 | 4/2019 | Siemionow et al. | |
| 2019/0130575 A1 | 5/2019 | Chen et al. | |
| 2019/0142519 A1 | 5/2019 | Siemionow et al. | |
| 2019/0192230 A1 | 6/2019 | Siemionow et al. | |
| 2019/0201106 A1 | 7/2019 | Siemionow et al. | |
| 2019/0307513 A1 | 10/2019 | Leung et al. | |
| 2019/0333626 A1 | 10/2019 | Mansi et al. | |
| 2020/0051274 A1 | 2/2020 | Siemionow et al. | |
| 2020/0151507 A1 | 5/2020 | Siemionow et al. | |
| 2020/0229877 A1 | 7/2020 | Siemionow et al. | |
| 2020/0327721 A1 | 10/2020 | Siemionow et al. | |
| 2020/0410687 A1 | 12/2020 | Siemionow et al. | |
| 2021/0267698 A1 | 9/2021 | Siemionow et al. | |

FOREIGN PATENT DOCUMENTS

| | | |
|---|---|---|
| EP | 3 151 736 A2 | 4/2017 |
| EP | 3 221 809 A1 | 9/2017 |
| EP | 3 361 979 A1 | 8/2018 |
| EP | 3 432 263 A1 | 1/2019 |
| GB | 2 536 650 A | 9/2016 |
| WO | WO 2007/110820 A2 | 10/2007 |
| WO | WO 2007/115826 A2 | 10/2007 |
| WO | WO 2012/018560 A2 | 2/2012 |

(56) References Cited

FOREIGN PATENT DOCUMENTS

| WO | WO 2012/027574 A1 | 3/2012 |
|---|---|---|
| WO | WO 2014/036473 A1 | 3/2014 |
| WO | WO 2015/058816 A1 | 4/2015 |
| WO | WO 2016/010737 A2 | 1/2016 |
| WO | WO 2016/078919 A1 | 5/2016 |
| WO | WO 2017/003453 A1 | 1/2017 |
| WO | WO 2017/066373 A1 | 4/2017 |
| WO | WO 2017/091833 A1 | 6/2017 |
| WO | WO 2018/048575 A1 | 3/2018 |
| WO | WO 2018/052966 A1 | 3/2018 |
| WO | WO 2018/057564 A1 | 3/2018 |
| WO | WO 2018/063528 A1 | 4/2018 |
| WO | WO 2018/140415 A1 | 8/2018 |
| WO | WO 2019/005722 A1 | 1/2019 |
| WO | WO 2019/195926 A1 | 10/2019 |

OTHER PUBLICATIONS

Non-Final Office Action dated Sep. 16, 2019 for U.S. Appl. No. 16/059,061, 20 pages.
Non-Final Office Action dated Jul. 10, 2020 for U.S. Appl. No. 16/842,793, 23 pages.
Non-Final Office Action dated Oct. 28, 2020 for U.S. Appl. No. 16/186,549, 30 pages.
Non-Final Office Action dated Oct. 27, 2020 for U.S. Appl. No. 16/537,645, 18 pages.
Extended European Search Report dated Oct. 25, 2017 for European Application No. 17186306.1, 14 pages.
Extended European Search Report dated Oct. 27, 2017 for European Application No. 17186307.9, 15 pages.
Extended European Search Report dated Feb. 16, 2018 for European Application No. 17195826.7, 8 pages.
Extended European Search Report dated Feb. 12, 2018 for European Application No. 17201224.7, 14 pages.
Extended European Search Report dated Feb. 27, 2018 for European Application No. 17206558.3, 13 pages.
Communication Pursuant to Article 94(3) dated Mar. 18, 2020 for European Application No. 17206558.3, 11 pages.
Extended European Search Report dated Apr. 17, 2019 for European Application No. 18211806.7, 8 pages.
Communication Pursuant to Article 94(3) dated Apr. 22, 2020 for European Application No. 18211806.7, 6 pages.
Extended European Search Report dated Jul. 5, 2018 for European Application No. 18150376.4, 10 pages.
Extended European Search Report dated Feb. 26, 2019 for European Application No. 18188557.5, 9 pages.
Extended European Search Report dated Feb. 1, 2019 for European Application No. 18205207.6, 9 pages.
Extended European Search Report dated Nov. 4, 2019 for European Application No. 19169136.9, 5 pages.
Extended European Search Report dated Oct. 23, 2019 for European Application No. 19179411.4, 8 pages.
Chen, H. et al., "Low-dose CT denoising with convolutional neural network," 2017 IEEE 14th International Symposium on Biomedical Imaging (Apr. 2017), 4 pages; doi:10.1109/ISBI.2017.7950488.
Christ, P. F. et al., "Automatic Liver and Lesion Segmentation in CT Using Cascaded Fully Convolutional Neural Networks and 3D Conditional Random Fields," Oct. 7, 2016, 8 pages; arXiv:1610.02177v1.
Egmont-Petersen, M. & Arts, T., "Recognition of radiopaque markers in X-ray images using a neural network as nonlinear filter," Pattern Recognition Letters, 20:521-533 (1999).
Fitzpatrick, J. M., "The role of registration in accurate surgical guidance," Proceedings of the Institute of Mechanical Engineering Medicine, Part H: Journal of Engineering in Medicine, 224(5):607-622 (2010); doi:10.1243/09544119JEIM589.

Gros, C. et al., "Automatic segmentation of the spinal cord and intramedullary multiple sclerosis lesions with convolutional neural networks," Neuroimage, 184:901-915 (2019).
Han, Z. et al., "Spine-GAN: Semantic segmentation of multiple spinal structures," Med Image Anal., 50:23-35 (2018); doi:10.1016/j.media.2018.08.005. Epub Aug. 25, 2018.
Jiménez-Pastor, A. et al., "Automatic localization and identification of vertebrae in spine CT scans by combining Deep Learning with morphological image processing techniques," European Congress of Radiology (ECR) 2018, Mar. 4, 2018, retrieved from the Internet at: https://quibim.com/wp-content/uploads/2018/03/3_ECR2018_AJP, 30 pages.
Krinninger, M., "Ein System zur Endoskopführung in der HNO-Chirurgie," Dissertation, Mar. 15, 2011, XP055450605, Technischen Universitat München; retrieved on Feb. 13, 2018 from https://mediatum.ub.tum.de/doc/998215/998215.pdf.—English Abstract, 1 page.
Krishnan, R. et al., "Automated Fiducial Marker Detection for Patient Registration in Image-Guided Neurosurgery," Computer Aided Surgery, 8(1):17-23 (2003).
Liu, Yanfeng et al., "Human-Readable Fiducial Marker Classification using Convolutional Neural Networks," 2017 IEEE International Conference on Electro Information Technology (EIT), IEEE, May 14, 2017, 5 pages.
Lootus, M. et al., "Vertebrae Detection and Labelling in Lumbar MR Images," Jan. 1, 2014, 12 pages.
Mao, X. -J. et al., "Image Restoration Using Very Deep Convolutional Encoder-Decoder Networks with Symmetric Skip Connections," 29th Conference on Neural Information Processing Systems (NIPS 2016), Barcelona, Spain, 9 pages.
Shi, R. et al., "An Efficient Method for Segmentation of MRI Spine Images," IEEE/ICME International Conference on Complex Medical Engineering, Jun. 2007, 6 pages; doi: 10.1109/ICCME.2007.4381830.
Song, Yuheng & Hao, Yan, "Image Segmentation Algorithms Overview," Jul. 7, 2017, retrieved from the Internet at: https://arxiv.org/ftp/arxiv/papers/1707/1707.02051, 6 pages.
Yang, D. et al., "Deep Image-to-Image Recurrent Network with Shape Basis Learning for Automatic Vertebra Labeling in Large-Scale 3D CT Volumes," Conference: International Conference on Medical Image Computing and Computer-Assisted Intervention, doi: 10.1007/978-3-319-66179-7_57, Sep. 2017, 9 pages.
Justin Cramer "Medical Image Segmentation and Design Tutorial with MevisLab" Apr. 27, 2016, XP054978063, URL: https://www.youtube.com/watch?v-PHf3Np37zTw retrieved on Jan. 26, 2018.
C. Cernazanu-Glavan et al. "Segmentation of Bone Structure in X-ray Images using Convolution Neural Network" Advances in Electrical and Computer Engineering vol. 13, No. 1, Jan. 1, 2013, pp. 87-94, XP055446296 ISSN: 1582-7445, DOI: 10.4316/AECE.2013.01015.
Maximilian Krinninger "Ein System zur Endoskopfuhrung in der HNO-Chirurgie (Disseration)" Mar. 15, 2011, XP055450605, Technische Universitat Munchen. URL: https://mediatum.ub.tum.de/doc/998215/998215.pdf retrieved Feb. 13, 2018.
Final Office Action dated Jun. 24, 2021 for U.S. Appl. No. 16/101,459, 40 pages.
Non-Final Office Action dated Oct. 4, 2021 for U.S. Appl. No. 17/145,178, 22 pages.
Non-Final Office Action dated Mar. 25, 2021 for U.S. Appl. No. 16/217,061, 25 pages.
Final Office Action dated Oct. 4, 2021 for U.S. Appl. No. 16/217,061, 68 pages.
Final Office Action dated Jun. 15, 2021 for U.S. Appl. No. 16/537,645, 13 pages.
Esfandiari, H. et al., "A deep learning framework for segmentation and pose estimation of pedicle screw implants based on C-arm fluoroscopy," International Journal of Computer Assisted Radiology and Surgery, 13:1269-1282 (2018).

* cited by examiner

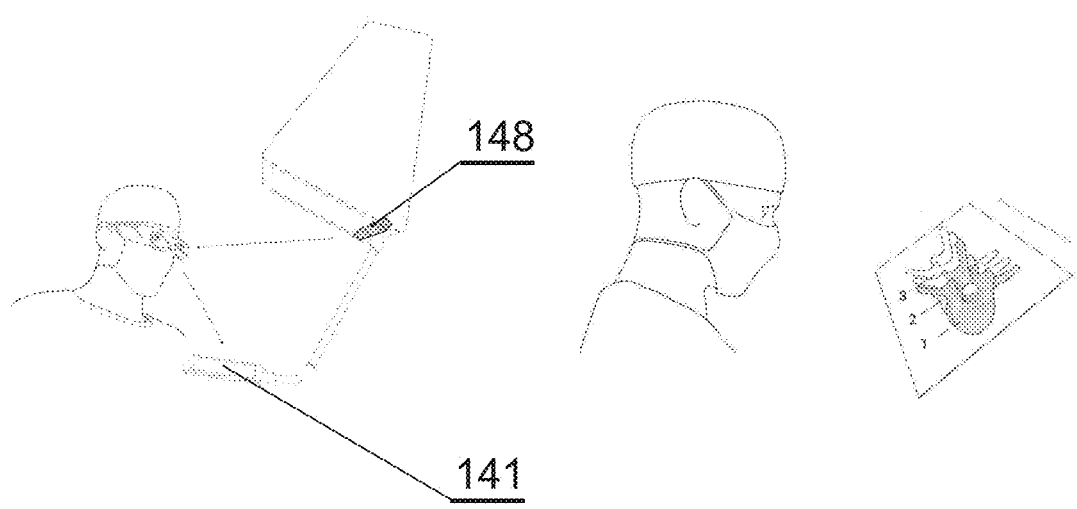
Fig. 5A                         Fig. 5B

GRAPHICAL USER INTERFACE FOR USE IN A SURGICAL NAVIGATION SYSTEM WITH A ROBOT ARM

TECHNICAL FIELD

The present disclosure relates to graphical user interfaces for use in surgical navigation systems with a robot arm, in particular to a system and method for operative planning and real time execution of a surgical procedure including the use of the robot arm.

BACKGROUND

Some of the typical functions of a computer-assisted surgery (CAS) system with navigation include presurgical planning of a procedure and presenting preoperative diagnostic information and images in useful formats. The CAS system presents status information about a procedure as it takes place in real time, displaying the preoperative plan along with intraoperative data. The CAS system may be used for procedures in traditional operating rooms, interventional radiology suites, mobile operating rooms or outpatient clinics. The procedure may be any medical procedure, whether surgical or non-surgical.

Surgical navigation systems are used to display the position and orientation of surgical instruments and medical implants with respect to presurgical or intraoperative medical imagery datasets of a patient. These images include pre and intraoperative images, such as two-dimensional (2D) fluoroscopic images and three-dimensional (3D) magnetic resonance imaging (MRI) or computed tomography (CT).

Navigation systems locate markers attached or fixed to an object, such as surgical instruments and patient. Most commonly these tracking systems are optical and electromagnetic. Optical tracking systems have one or more stationary cameras that observe passive reflective markers or active infrared LEDs attached to the tracked instruments or the patient. Eye-tracking solutions are specialized optical tracking systems that measure gaze and eye motion relative to a user's head. Electromagnetic systems have a stationary field generator that emits an electromagnetic field that is sensed by coils integrated into tracked medical tools and surgical instruments.

SUMMARY OF THE INVENTION

Incorporating image segmentation processes that automatically identify various bone landmarks, based on their density, can increase planning accuracy. One such bone landmark is the spinal pedicle, which is made up of dense cortical bone making its identification utilizing image segmentation easier. The pedicle is used as an anchor point for various types of medical implants. Achieving proper implant placement in the pedicle is heavily dependent on the trajectory selected for implant placement. Ideal trajectory is identified by surgeon based on review of advanced imaging (e.g., CT or MRI), goals of the surgical procedure, bone density, presence or absence of deformity, anomaly, prior surgery, and other factors. The surgeon then selects the appropriate trajectory for each spinal level. Proper trajectory generally involves placing an appropriately sized implant in the center of a pedicle. Ideal trajectories are also critical for placement of inter-vertebral biomechanical devices.

Another example is placement of electrodes in the thalamus for the treatment of functional disorders, such as Parkinson's. The most important determinant of success in patients undergoing deep brain stimulation surgery is the optimal placement of the electrode. Proper trajectory is defined based on preoperative imaging (such as MRI or CT) and allows for proper electrode positioning.

Another example is minimally invasive replacement of prosthetic/biologic mitral valve in for the treatment of mitral valve disorders, such as mitral valve stenosis or regurgitation. The most important determinant of success in patients undergoing minimally invasive mitral valve surgery is the optimal placement of the three dimensional valve.

The fundamental limitation of surgical navigation systems is that they provide restricted means of communicating to the surgeon. Currently-available navigation systems present some drawbacks.

Typically, one or several computer monitors are placed at some distance away from the surgical field. They require the surgeon to focus the visual attention away from the surgical field to see the monitors across the operating room. This results in a disruption of surgical workflow. Moreover, the monitors of current navigation systems are limited to displaying multiple slices through three-dimensional diagnostic image datasets, which are difficult to interpret for complex 3D anatomy.

The fact that the screen of the surgical navigation system is located away from the region of interest (ROI) of the surgical field requires the surgeon to continuously look back and forth between the screen and the ROI. This task is not intuitive and results in a disruption to surgical workflow and decreases planning accuracy.

When defining and later executing an operative plan, the surgeon interacts with the navigation system via a keyboard and mouse, touchscreen, voice commands, control pendant, foot pedals, haptic devices, and tracked surgical instruments. Based on the complexity of the 3D anatomy, it can be difficult to simultaneously position and orient the instrument in the 3D surgical field only based on the information displayed on the monitors of the navigation system. Similarly, when aligning a tracked instrument with an operative plan, it is difficult to control the 3D position and orientation of the instrument with respect to the patient anatomy. This can result in an unacceptable degree of error in the preoperative plan that will translate to poor surgical outcome.

There are known surgical robot arms which may operate some of the surgical instruments used during the operation. However, a robot arm is a relatively large structure and may obstruct the operative field.

There is disclosed a surgical navigation system comprising: a tracker for real-time tracking of a position and orientation of a robot arm a surgeon's head, a 3D display system and a patient anatomy to provide current position and orientation data; a source of a patient anatomical data and a robot arm virtual image; a surgical navigation image generator configured to generate a surgical navigation image comprising the patient anatomy and the robot arm virtual image in accordance to the current position and orientation data provided by the tracker; and a 3D display system configured to show the surgical navigation image.

The display of the robot arm virtual image may be configurable such that it can be selectively visible or hidden.

The display of the robot arm virtual image may be configurable such that its opacity can be adjusted.

The patient anatomical data may comprise a three-dimensional reconstruction of a segmented model comprising at least two sections representing parts of the anatomy; and wherein the display of the patient anatomy is configurable such that at least one section of the anatomy is displayed and at least one other section of the anatomy is not displayed.

The system may further comprise a source of at least one of: an operative plan and a virtual surgical instrument model; wherein the tracker is further configured for real-time tracking of surgical instruments; wherein the surgical navigation image further comprises a three-dimensional image representing a virtual image of the surgical instruments.

The system may further comprise a source of information about suggested positions and/or orientations of the surgical instruments, and the virtual image of the surgical instruments may be configured to indicate the suggested positions and/or orientations of the surgical instruments according to the operative plan data.

The three-dimensional image of the surgical navigation image may further comprise a graphical cue indicating the required change of position and orientation of the surgical instrument to match the suggested position and orientation according to the pre-operative plan data.

The surgical navigation image may further comprise a set of orthogonal (axial, sagittal, and coronal) and/or arbitrary planes of the patient anatomical data.

The 3D display system may be configured to show the surgical navigation image at a see-through device, and wherein the tracker may be configured for real-time tracking of the position and orientation of the see-through device such that an augmented reality image collocated with the patient anatomy in the surgical field underneath the see-through device is visible to a viewer looking from above the see-through device towards the surgical field.

The patient anatomical data may comprise output data of a semantic segmentation process of an anatomy scan image.

The system may further comprise a convolutional neural network system configured to perform the semantic segmentation process to generate the patient anatomical data.

There is also disclosed a method for providing an augmented reality image during an operation, comprising: providing a source of a patient anatomical data and a robot arm virtual image; real-time tracking, by means of a tracker, a position and orientation of a robot arm, a surgeon's head, a 3D display system and a patient anatomy to provide current position and orientation data; generating, by a surgical navigation image generator, a surgical navigation image comprising the patient anatomy and the robot arm virtual image in accordance to the current position and orientation data provided by the tracker; and showing the surgical navigation image at a 3D display system.

These and other features, aspects and advantages of the invention will become better understood with reference to the following drawings, descriptions and claims.

BRIEF DESCRIPTION OF THE DRAWINGS

The surgical navigation system and method are presented herein by means of non-limiting example embodiments shown in a drawing, wherein:

FIG. 5A show eye tracking in accordance with an embodiment of the invention.

FIG. 5B show eye tracking in accordance with an embodiment of the invention.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention.

Figure 1A:
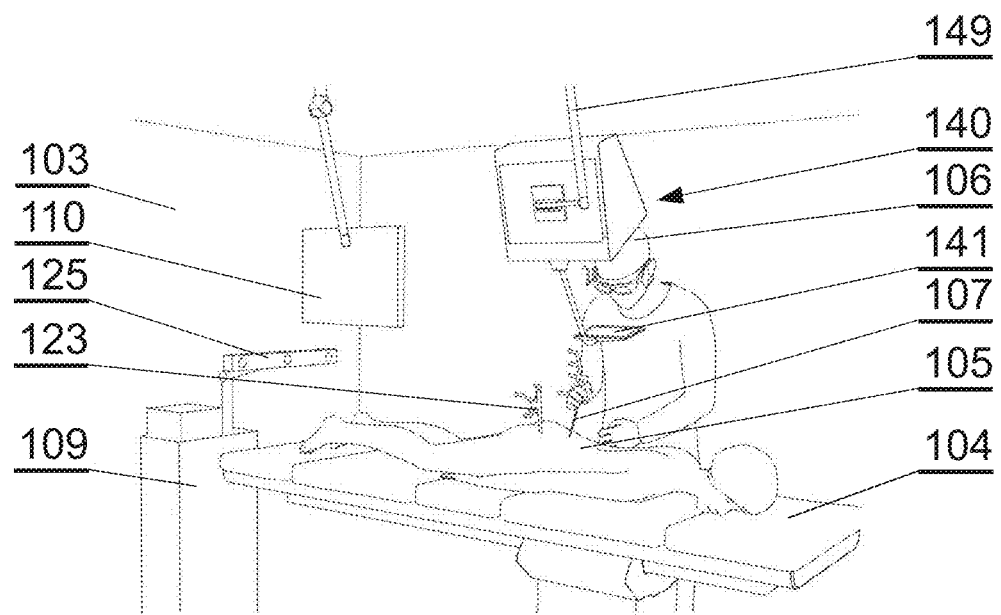
FIG. 1A shows a layout of a surgical room employing the surgical navigation system in accordance with an embodiment of the invention.
Figures 1B, 1C:
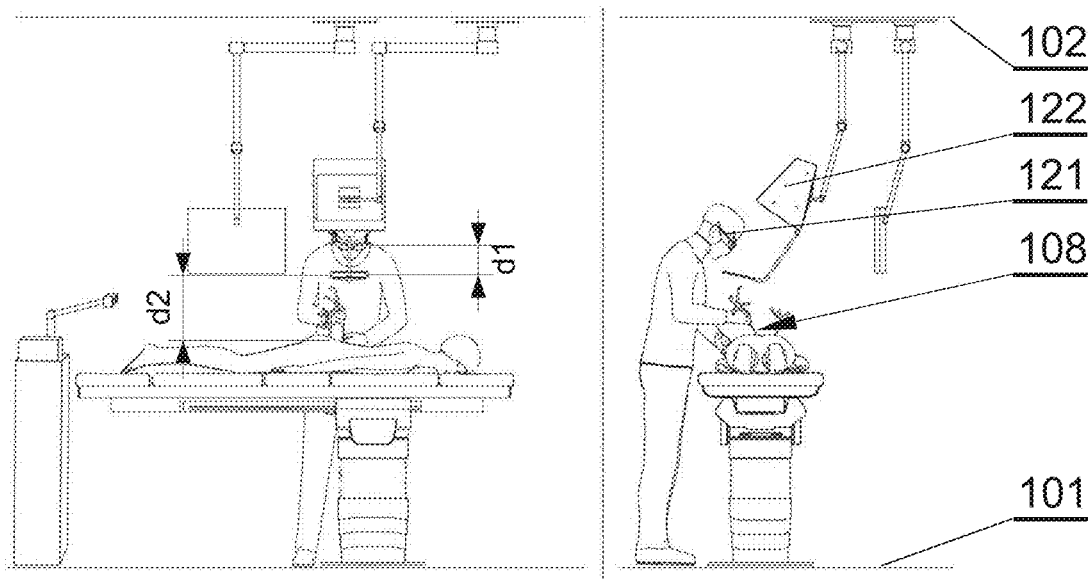
FIG. 1B shows a layout of a surgical room employing the surgical navigation system in accordance with an embodiment of the invention.
FIG. 1C shows a layout of a surgical room employing the surgical navigation system in accordance with an embodiment of the invention.

The system presented herein is comprises a 3D display system 140 to be implemented directly on real surgical applications in a surgical room as shown in FIGS. 1A-1C. The 3D display system 140 as shown in the example embodiment comprises a 3D display 142 for emitting a surgical navigation image 142A towards a see-through mirror 141 that is partially transparent and partially reflective, such that an augmented reality image 141A collocated with the patient anatomy in the surgical field 108 underneath the see-through mirror 141 is visible to a viewer looking from above the see-through mirror 141 towards the surgical field 108.

The surgical room typically comprises a floor 101 on which an operating table 104 is positioned. A patient 105 lies on the operating table 104 while being operated by a surgeon 106 with the use of various surgical instruments 107. The surgical navigation system as described in details below can have its components, in particular the 3D display system 140, mounted to a ceiling 102, or alternatively to the floor 101 or a side wall 103 of the operating room. Furthermore, the components, in particular the 3D display system 140, can be mounted to an adjustable and/or movable floor-supported structure (such as a tripod). Components other than the 3D display system 140, such as the surgical image generator 131, can be implemented in a dedicated computing device 109, such as a stand-alone PC computer, which may have its own input controllers and display(s) 110.

In general, the system is designed for use in such a configuration wherein the distance d1 between the surgeon's eyes and the see-through mirror 141, is shorter than the distance d2, between the see-through mirror 141 and the operative field at the patient anatomy 105 being operated.

In addition, the system comprises a robot arm 191 for handling some of the surgical tools. The robot arm 191 may have two closed loop control systems: its own position system and one used with the optical tracker as presented herein. Both systems of control may work together to ensure that the robot arm is on the right position. The robot arm's position system may comprise encoders placed at each joint to determine the angle or position of each element of the arm. The second system may comprise a robot arm marker array 126 attached to the robot arm to be tracked by the tracker 125, as described below. Any kind of surgical robotic system can be used, preferably one that follows standards of the U.S. Food & Drug Administration.

Figure 2A:
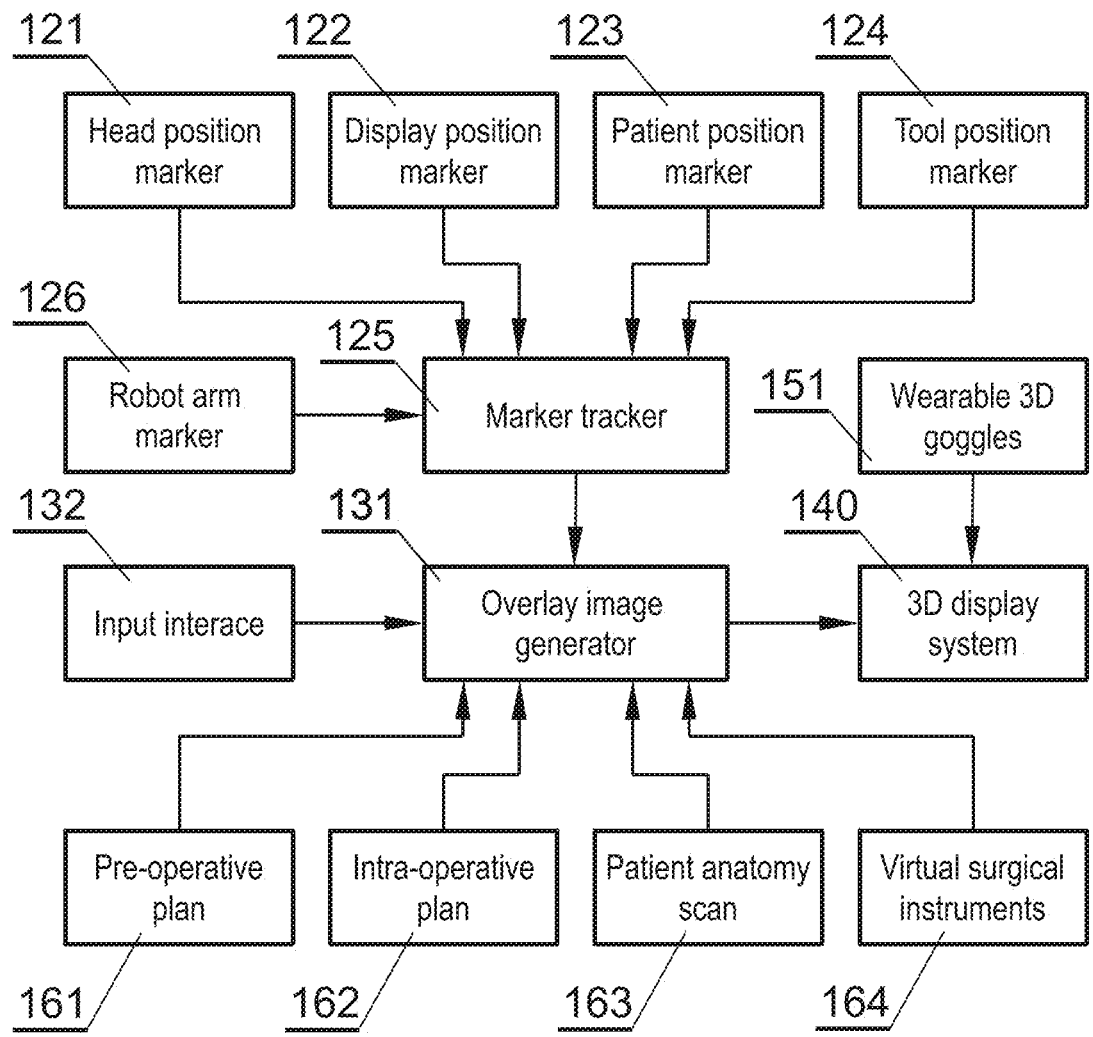
FIG. 2A shows components of the surgical navigation system in accordance with an embodiment of the invention.
Figure 2B:
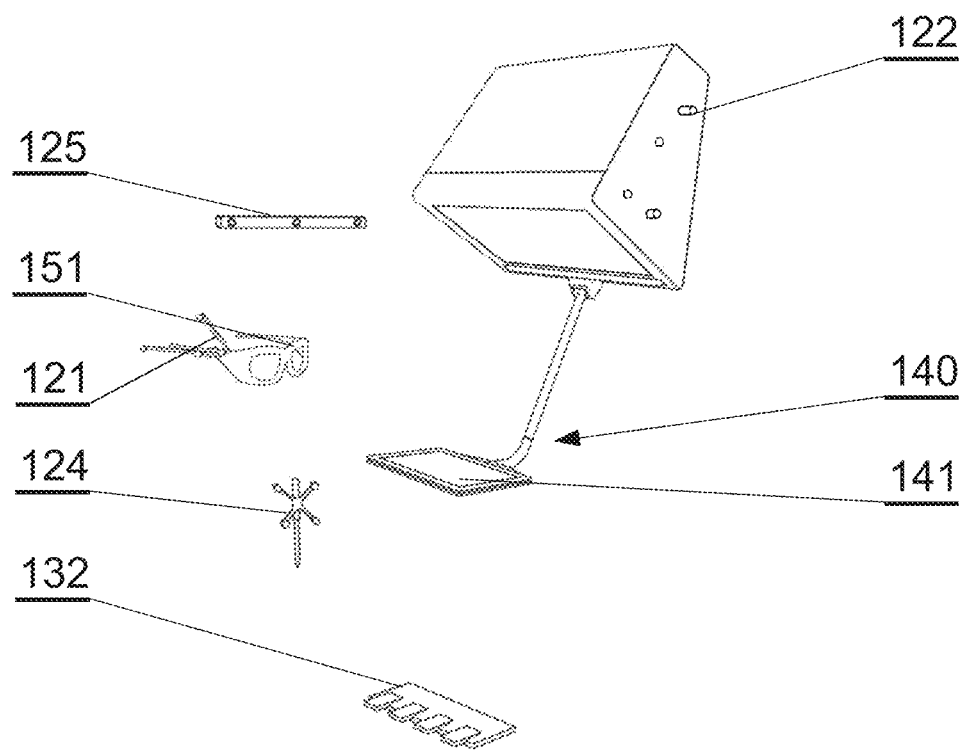
FIG. 2B shows components of the surgical navigation system in accordance with an embodiment of the invention.

FIG. 2A shows a functional schematic presenting connections between the components of the surgical navigation system and FIG. 2B shows examples of physical embodiments of various components.

The surgical navigation system comprises a tracking system for tracking in real time the position and/or orientation of various entities to provide current position and/or orientation data. For example, the system may comprise a plurality of arranged fiducial markers, which are trackable by a fiducial marker tracker 125. Any known type of tracking system can be used. For example in case of a marker tracking system, 4-point marker arrays are tracked by a three-camera sensor to provide movement along six degrees of freedom. A head position marker array 121 can be attached to the surgeon's head for tracking of the position and orientation of the surgeon and the direction of gaze of the surgeon—for example, the head position marker array 121 can be integrated with the wearable 3D glasses 151 or can be attached to a strip worn over the surgeon's head.

A display marker array 122 can be attached to the see-through mirror 141 of the 3D display system 140 for tracking its position and orientation, as the see-through mirror 141 is movable and can be placed according to the current needs of the operative setup.

A patient anatomy marker array 123 can be attached at a particular position and orientation of the anatomy of the patient.

A surgical instrument marker array 124 can be attached to the instrument whose position and orientation shall be tracked.

A robot arm marker array 126 can be attached to at least one robot arm 191 to track its position.

Preferably, the markers in at least one of the marker arrays 121-124 are not coplanar, which helps to improve the accuracy of the tracking system.

Therefore, the tracking system comprises means for real-time tracking of the position and orientation of at least one of: a surgeon's head 106, a 3D display 142, a patient anatomy 105, and surgical instruments 107. Preferably, all of these elements are tracked by a fiducial marker tracker 125.

A surgical navigation image generator 131 is configured to generate an image to be viewed via the see-through mirror 141 of the 3D display system. It generates a surgical navigation image 142A comprising data of at least one of: the pre-operative plan 161 (which are generated and stored in a database before the operation), data of the intra-operative plan 162 (which can be generated live during the operation), data of the patient anatomy scan 163 (which can be generated before the operation or live during the operation) and virtual images 164 of surgical instruments used during the operation (which are stored as 3D models in a database), as well as virtual image 166 of the robot arm 191.

The surgical navigation image generator 131, as well as other components of the system, can be controlled by a user (i.e. a surgeon or support staff) by one or more user interfaces 132, such as foot-operable pedals (which are convenient to be operated by the surgeon), a keyboard, a mouse, a joystick, a button, a switch, an audio interface (such as a microphone), a gesture interface, a gaze detecting interface etc. The input interface(s) are for inputting instructions and/or commands.

All system components are controlled by one or more computers which are/is controlled by an operating system and one or more software applications. The computer may be equipped with a suitable memory which may store computer program or programs executed by the computer in order to execute steps of the methods utilized in the system. Computer programs are preferably stored on a non-transitory medium. An example of a non-transitory medium is a non-volatile memory, for example a flash memory while an example of a volatile memory is RAM. The computer instructions are executed by a processor. These memories are exemplary recording media for storing computer programs comprising computer-executable instructions performing all the steps of the computer-implemented method according the technical concept presented herein. The computer(s) can be placed within the operating room or outside the operating room. Communication between the computer(s) and the components of the system may be performed by wire or wirelessly, according to known communication means.

Figure 3A:
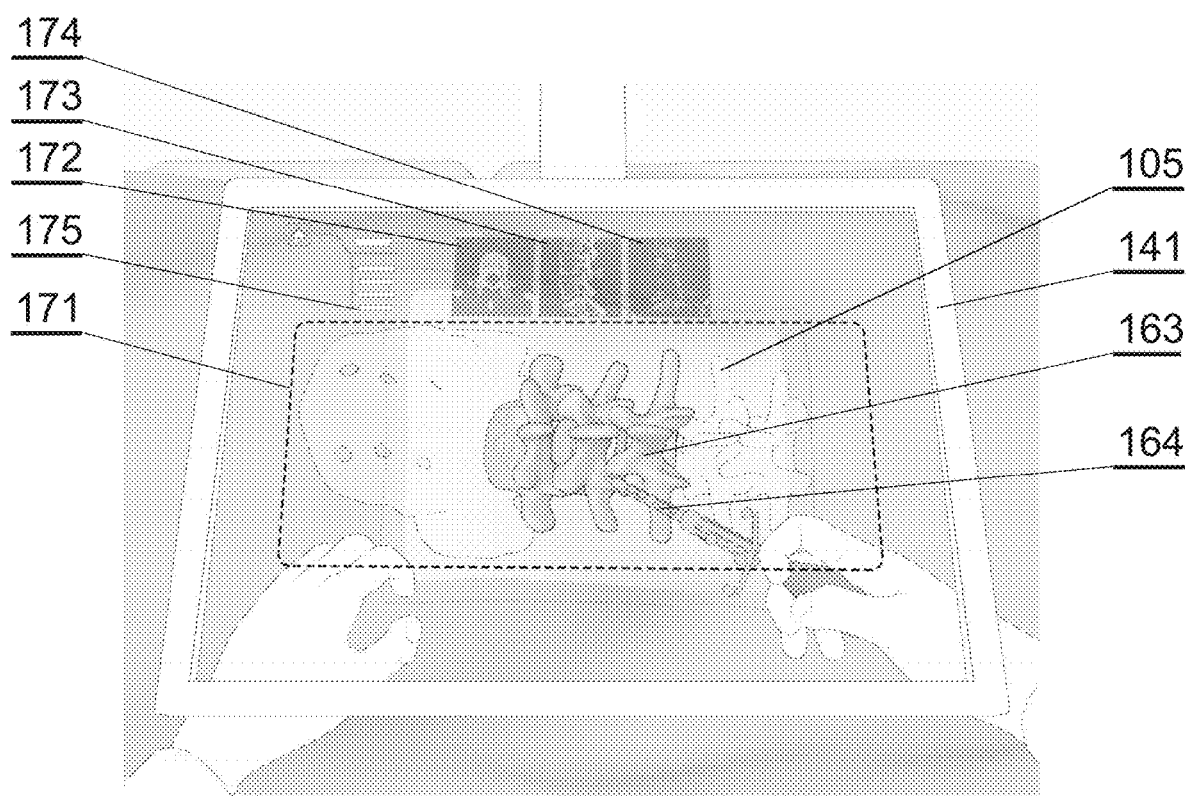
FIG. 3A shows an example of an augmented reality display in accordance with an embodiment of the invention.
Figure 3B:
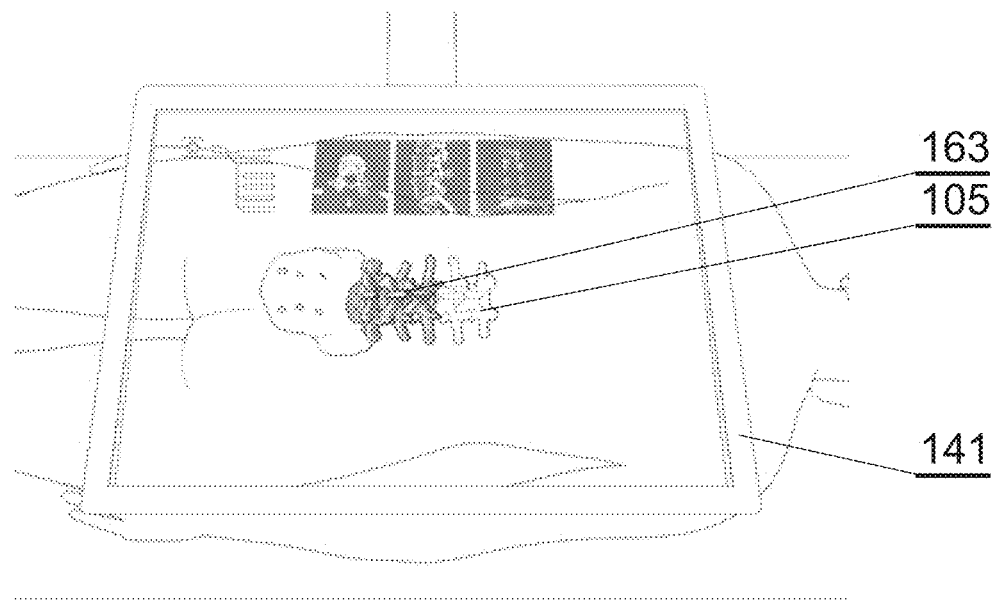
FIG. 3B shows an example of an augmented reality display in accordance with an embodiment of the invention.
Figure 3C:
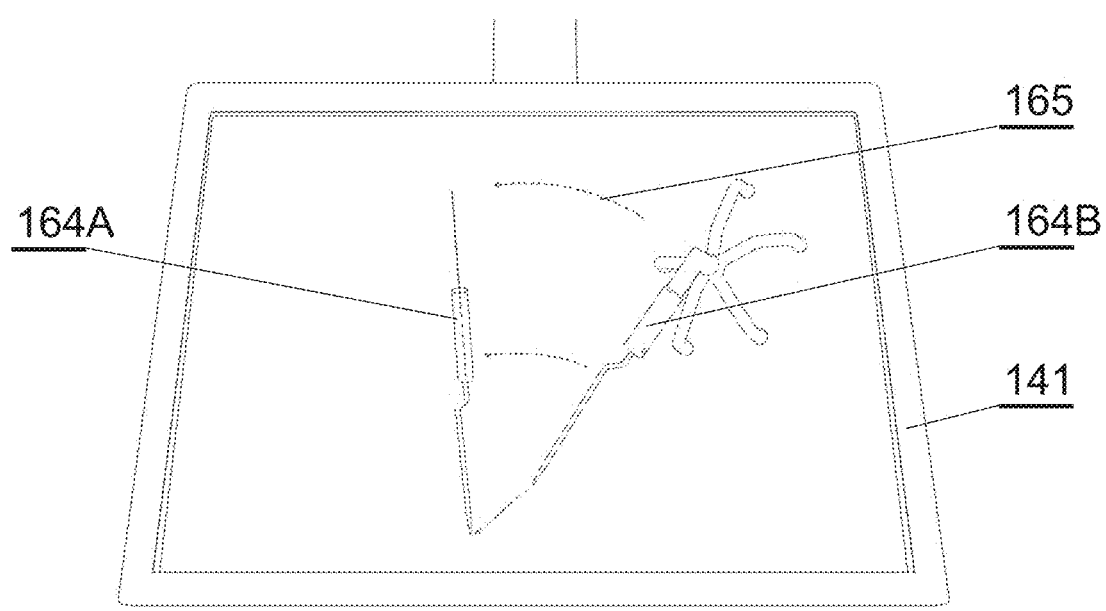
FIG. 3C shows an example of an augmented reality display in accordance with an embodiment of the invention.
Figure 3D:
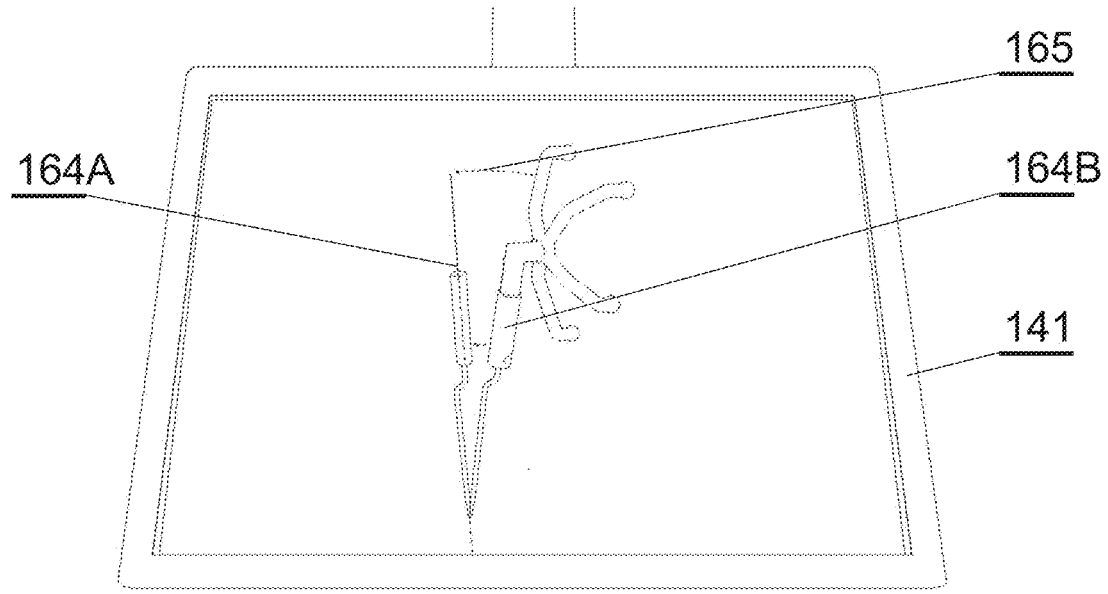
FIG. 3D shows an example of an augmented reality display in accordance with an embodiment of the invention.
Figure 3E:
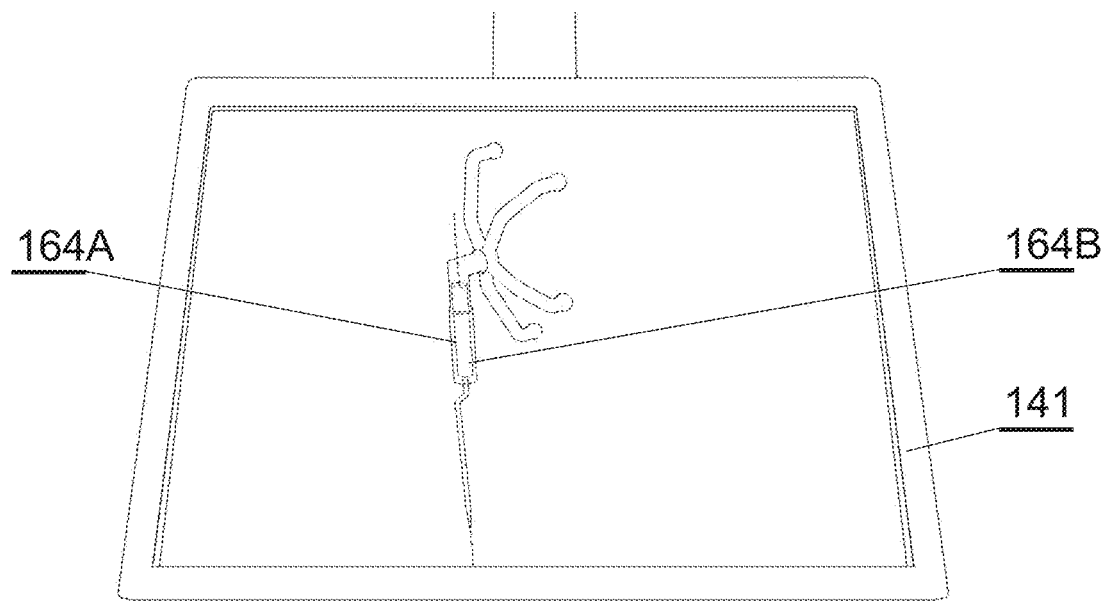
FIG. 3E shows an example of an augmented reality display in accordance with an embodiment of the invention.
Figure 3F:
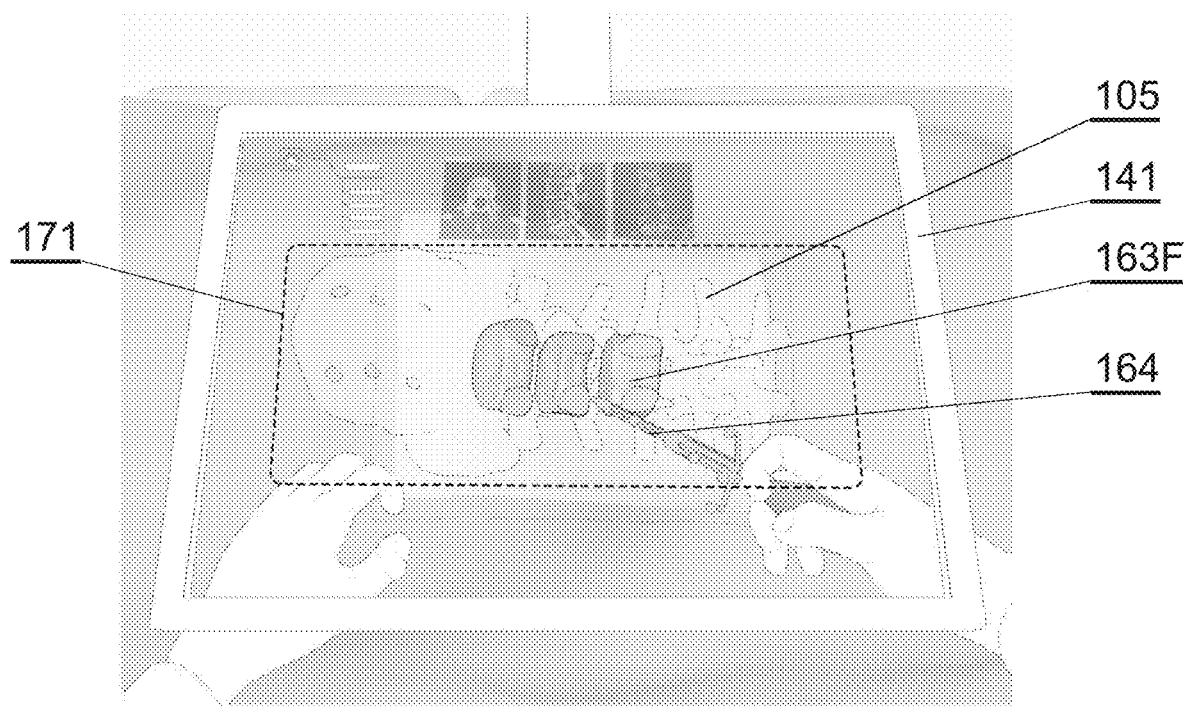
FIG. 3F shows an example of an augmented reality display in accordance with an embodiment of the invention.
Figure 3G:
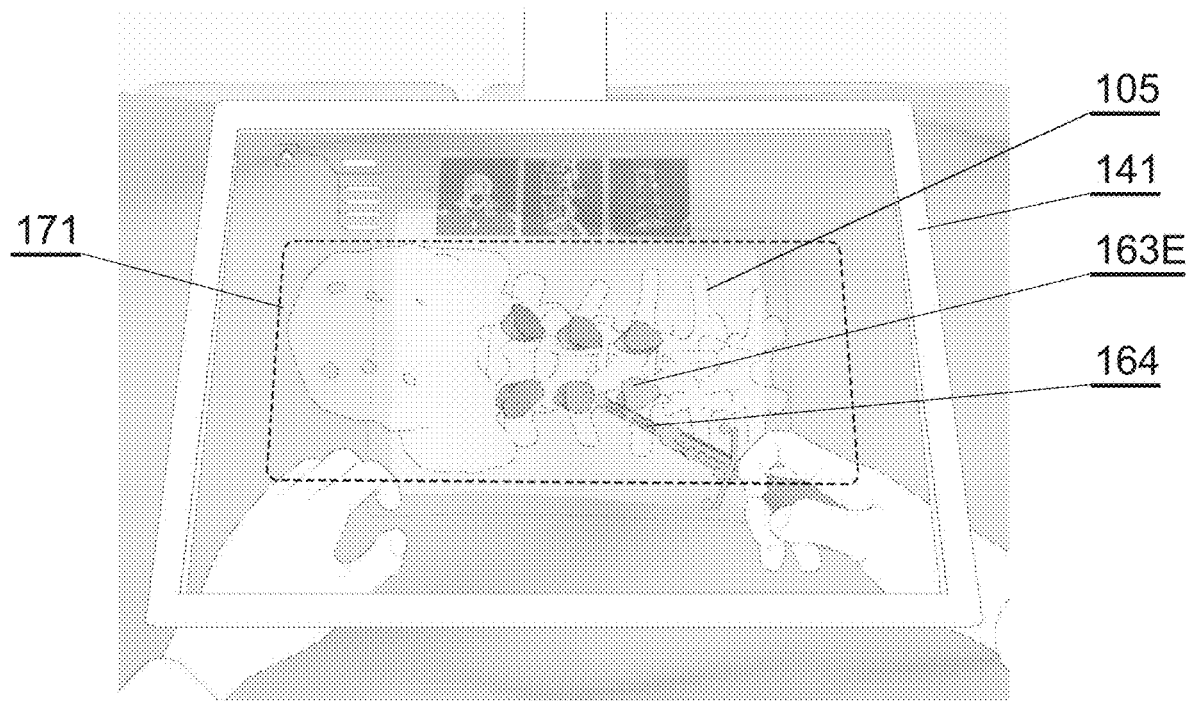
FIG. 3G shows an example of an augmented reality display in accordance with an embodiment of the invention.
Figure 3H:
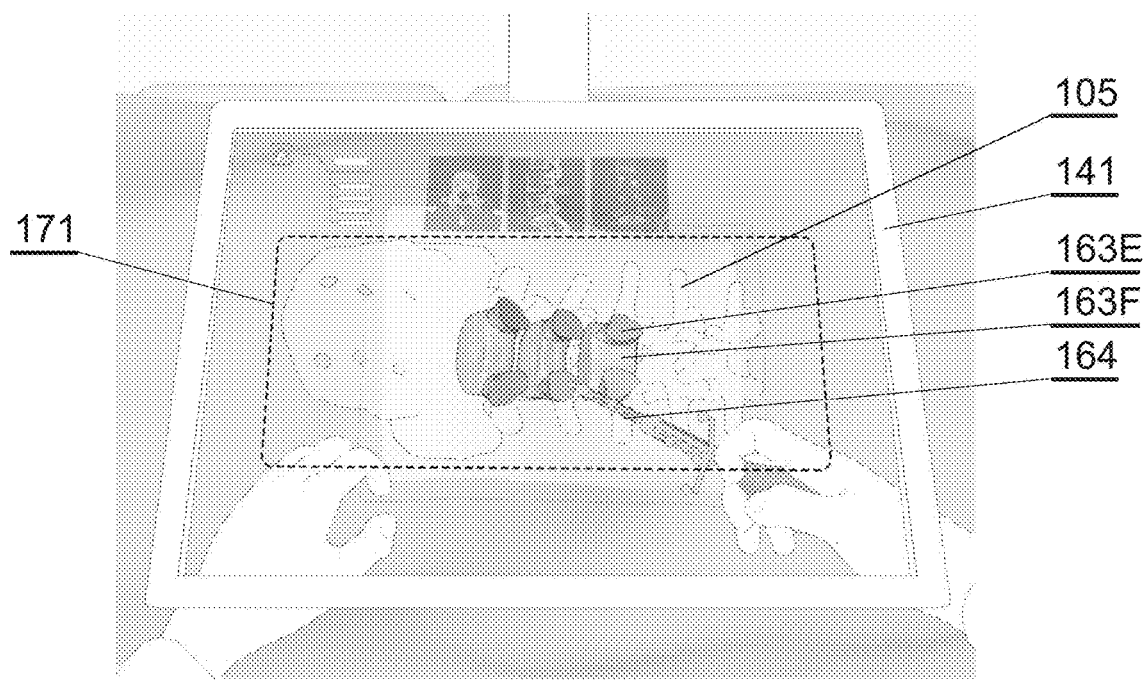
FIG. 3H shows an example of an augmented reality display in accordance with an embodiment of the invention.
Figure 3I:
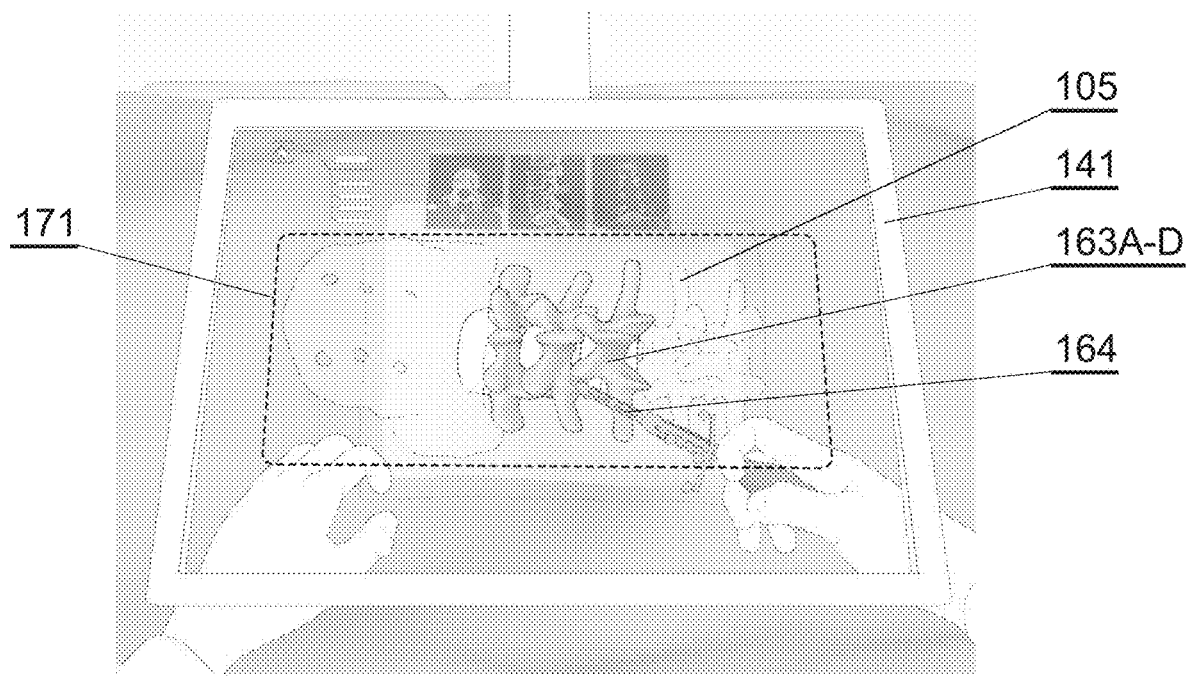
FIG. 3I shows an example of an augmented reality display in accordance with an embodiment of the invention.
Figure 3J:
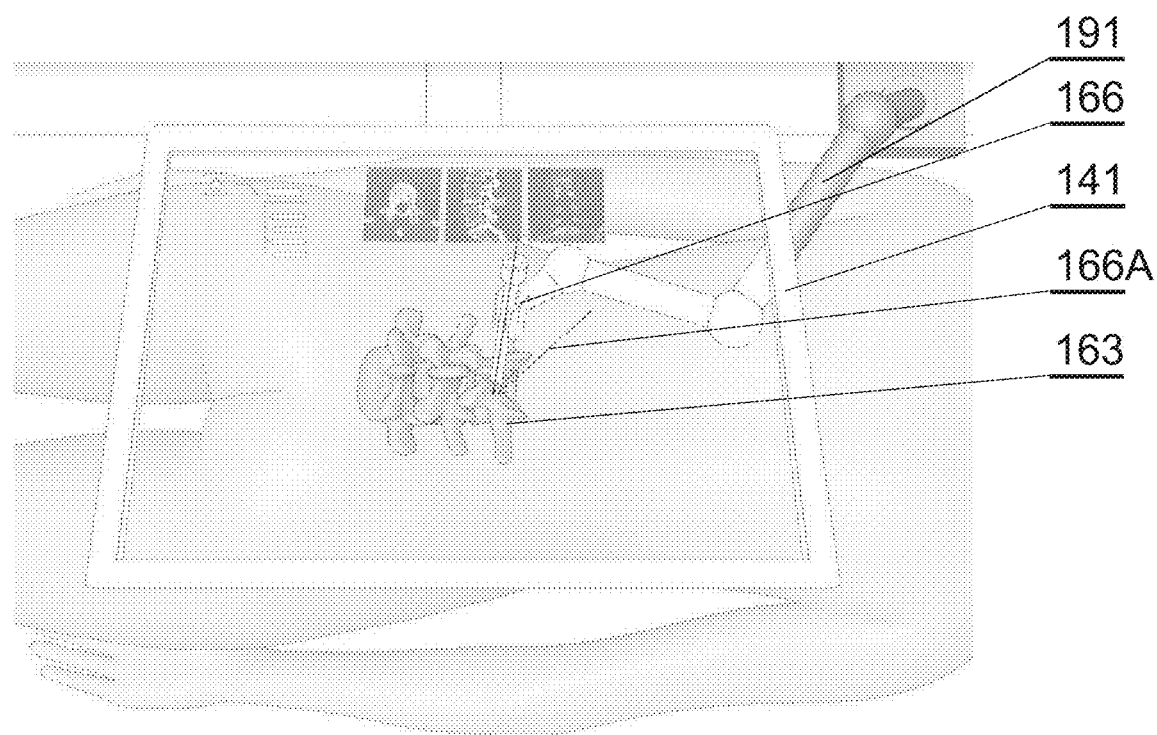
FIG. 3J shows an example of an augmented reality display in accordance with an embodiment of the invention.

The aim of the system in some embodiments is to generate, via the 3D display system 140, an augmented reality image such as shown in FIG. 3J, and also possibly 3A-3I. When the surgeon looks via the 3D display system 140, the surgeon sees the augmented reality image 141A which comprises:
- the real world image: the patient anatomy, surgeon's hands and the instrument currently in use (which may be partially inserted into the patient's body and hidden under the skin);
- and a computer-generated surgical navigation image 142A comprising the patient anatomy 163 and a virtual image 166 of the robot arm.

As a result, the augmented reality image comprises a virtual image 166 of the robot arm collocated with the real physical anatomy of the patient, as shown in FIG. 3B. Furthermore, the augmented reality image may comprise a guidance image 166A that indicates, according to the pre-operative plan data, the suggested position and orientation of the robot arm 191.

The virtual image 166 of the robot arm may be configurable such that it can be selectively displayed or hidden, in full or in part (for example, some parts of the robot arm can be hidden (such as the forearm) and some (such as the surgical tool holder) can be visible). Moreover, the opacity of the robot arm virtual image 166 can be selectively changed, such that it does not obstruct the patient anatomy.

The display of the patient anatomy 163 can be configurable, such that at least one section of the anatomy 163A-

163F is displayed and at least one other section of the anatomy 163A-163F is not displayed, as shown in FIGS. 3F-3I.

Furthermore, the surgical navigation image may further comprise a 3D image 171 representing at least one of: the virtual image of the instrument 164 or surgical guidance indicating suggested (ideal) trajectory and placement of surgical instruments 107, according to the pre-operative plans 161 (as shown in FIG. 3C); preferably, three different orthogonal planes of the patient anatomical data 163: coronal 174, sagittal 173, axial 172; preferably, a menu 175 for controlling the system operation.

If the 3D display 142 is stereoscopic, the surgeon shall use a pair of 3D glasses 151 to view the augmented reality image 141A. However, if the 3D display 142 is autostereoscopic, it may be not necessary for the surgeon to use the 3D glasses 151 to view the augmented reality image 141A.

The virtual image of the patient anatomy 163 is generated based on data representing a three-dimensional segmented model comprising at least two sections representing parts of the anatomy. The anatomy can be for example a bone structure, such as a spine, skull, pelvis, long bones, shoulder joint, hip joint, knee joint etc. This description presents examples related particularly to a spine, but a skilled person will realize how to adapt the embodiments to be applicable to the other bony structures or other anatomy parts as well.

Figure 6:
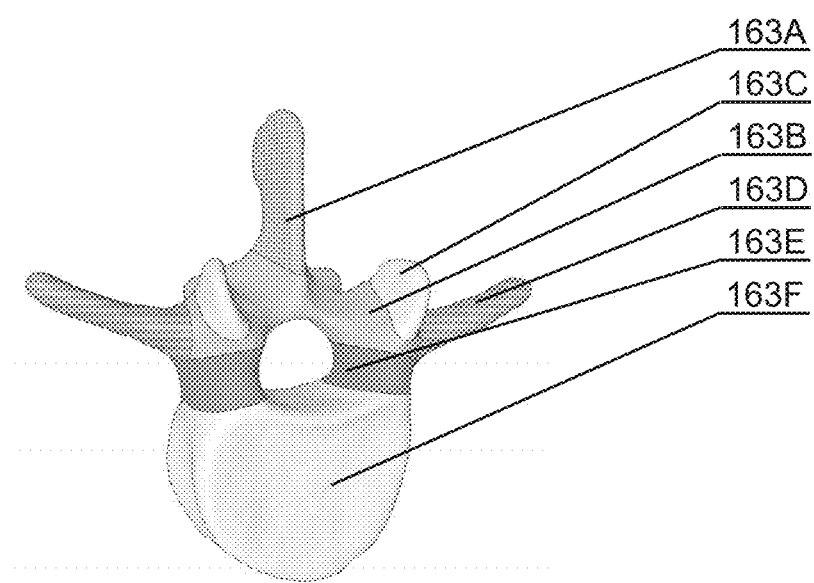
FIG. 6 shows a 3D representation of the results of the semantic segmentation on one vertebrae for use in an embodiment of the invention.

For example, the model can represent a spine, as shown in FIG. 6, with the following section: spinous process 163A, lamina 163B, articular process 163C, transverse process 163D, pedicles 163E, vertebral body 163F.

The model can be generated based on a pre-operative scan of the patient and then segmented manually by a user or automatically by a computer, using dedicated algorithms and/or neural networks, or in a hybrid approach including a computer-assisted manual segmentation. For example, a convolutional neural network can be employed.

Preferably, the images of the orthogonal planes 172, 173, 174 are displayed in an area next (preferably, above) to the area of the 3D image 171, as shown in FIG. 3A, wherein the 3D image 171 occupies more than 50% of the area of the see-through device 141.

The location of the images of the orthogonal planes 172, 173, 174 may be adjusted in real time depending on the location of the 3D image 171, when the surgeon changes the position of the head during operation, such as not to interfere with the 3D image 171.

Therefore, in general, the anatomical information of the user is shown in two different layouts that merge for an augmented and mixed reality feature. The first layout is the anatomical information that is projected in 3D in the surgical field. The second layout is in the orthogonal planes.

The surgical navigation image 142A is generated by the image generator 131 in accordance with the tracking data provided by the fiducial marker tracker 125, in order to superimpose the anatomy images and the instrument images exactly over the real objects, in accordance with the position and orientation of the surgeon's head. The markers are tracked in real time and the image is generated in real time. Therefore, the surgical navigation image generator 131 provides graphics rendering of the virtual objects (patient anatomy, surgical plan and instruments) collocated to the real objects according to the perspective of the surgeon's perspective.

For example, surgical guidance may relate to suggestions (virtual guidance clues 164) for placement of a pedicle screw in spine surgery or the ideal orientation of an acetabular component in hip arthroplasty surgery. These suggestions may take a form of animations that show the surgeon whether the placement is correct. The suggestions may be displayed both on the 3D holographic display and the orthogonal planes. The surgeon may use the system to plan these orientations before or during the surgical procedure.

In particular, the 3D image 171 is adapted in real time to the position and orientation of the surgeon's head. The display of the different orthogonal planes 172, 173, 174 may be adapted according to the current position and orientation of the surgical instruments used.

The aligning the line of sight of the surgeon onto the see-through mirror with the patient anatomy underneath the see-through mirror, involving the scaling and orientation of the image, can be realized based on known solutions in the field of computer graphics processing, in particular for virtual reality, including virtual scene generation, using well-known mathematical formulas and algorithms related to viewer centered perspective. For example, such solutions are known from various tutorials and textbooks (such as "The Future of the CAVE" by T. A. DeFanti et al, Central European Journal of Engineering, 2010, DOI: 10.2478/s13531-010-0002-5).

FIG. 3B shows an example indicating collocation of the virtual image of the patient anatomy 163 and the real anatomy 105.

For example, as shown in FIG. 3C, the 3D image 171 may demonstrate a mismatch between a supposed/suggested position of the instrument according to the pre-operative plan 161, displayed as a first virtual image of the instrument 164A located at its supposed/suggested position, and an actual position of the instrument, visible either as the real instrument via the see-through display and/or a second virtual image of the instrument 164B overlaid on the current position of the instrument. Additionally, graphical guiding cues, such as arrows 165 indicating the direction of the supposed change of position, can be displayed.

FIG. 3D shows a situation wherein the tip of the supposed position of the instrument displayed as the first virtual image 164A according to the pre-operative plan 161 matches the tip of the real surgical instrument visible or displayed as the second virtual image 164B. However, the remainder of objects do not match, therefore the graphical cues 165 still indicate the need to change position. The surgical instrument is close to the correct position and the system may provide information on how close the surgical instrument is to the planned position.

FIG. 3E shows a situation wherein the supposed position of the real surgical instrument matches the position of the instrument according to the pre-operative plan 161, i.e. the correct position for surgery. In this situation the graphical cues 165 are no longer displayed, but the virtual images 164A, 164B may be changed to indicate the correct position, e.g. by highlighting it or blinking.

In some situations, the image of the full patient anatomy 163, as shown in FIG. 3A, may be obstructive. To solve this problem, the system allows a selective display of the parts of the anatomy 163, such that at least one part of the anatomy is shown and at least one other part of the anatomy is not shown.

For example, the surgeon may only want to see isolated parts of the spinal anatomy during spine surgery (only vertebral body or only the pedicle). Each part of the spinal anatomy is displayed at the request of the surgeon. For example the surgeon may only want to see the virtual representation of the pedicle during placement of bony anchors. This would be advantageous, as it would not have any visual interference from the surrounding anatomical structures.

Therefore, a single part of the anatomy may be displayed, for example only the vertebral body 163F (FIG. 3F) or only the pedicles 163E (FIG. 3G). Alternatively, two parts of the anatomy may be displayed, for example the vertebral body 163F and the pedicles 163E (FIG. 3H); or a larger group of anatomy parts may be displayed, such as the top parts of 163A-D of the spine (FIG. 3I).

The user may select the parts that are to be displayed via the input interface 132.

For example, the GUI may comprise a set of predefined display templates, each template defining a particular part of the anatomy to be displayed (such as FIG. 3F, 3G) or a plurality of parts of the anatomy to be displayed (such as FIG. 3H, 3I). The user may then use a dedicated touch-screen button, keyboard key, pedal or other user interface navigation element to select a particular template to be displayed or to switch between consecutive templates.

Alternatively, the GUI may display a list of available parts of anatomy to be displayed and the user may select the parts to be displayed.

The GUI interface for configuring the parts that are to be displayed can be configured to be operated directly by the surgeon or by an assistant person.

The foregoing description will provide examples of a 3D display 142 with a see-through mirror 141, which is particularly effective to provide the surgical navigation data. However, other 3D display systems can be used as well to show the automatically segmented parts of anatomy, such as 3D head-mounted displays.

The see-through mirror (also called a half-silvered mirror) 141 is at least partially transparent and partially reflective, such that the viewer can see the real world behind the mirror but the mirror also reflects the surgical navigation image generated by the display apparatus located above it.

For example, a see-through mirror as commonly used in teleprompters can be used. For example, the see-through mirror 141 can have a reflective and transparent rate of 50 R/50 T, but other rates can be used as well.

The surgical navigation image is emitted from above the see-through mirror 141 by the 3D display 142.

Figure 4A:
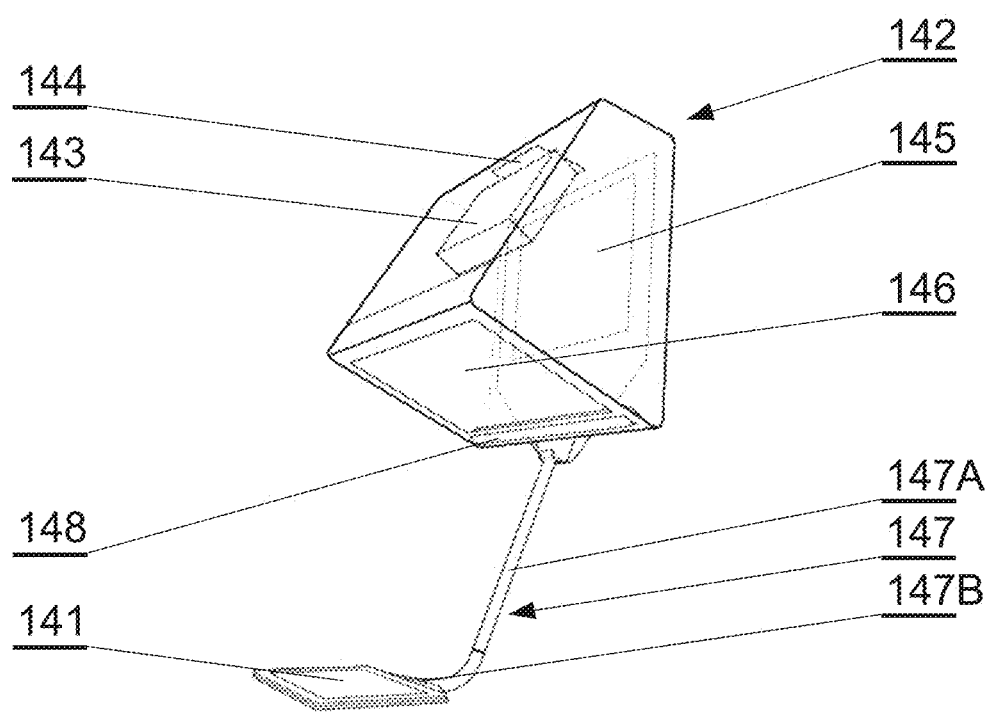
FIG. 4A shows an embodiment of a 3D display system for use in an embodiment of the invention.
Figure 4C:
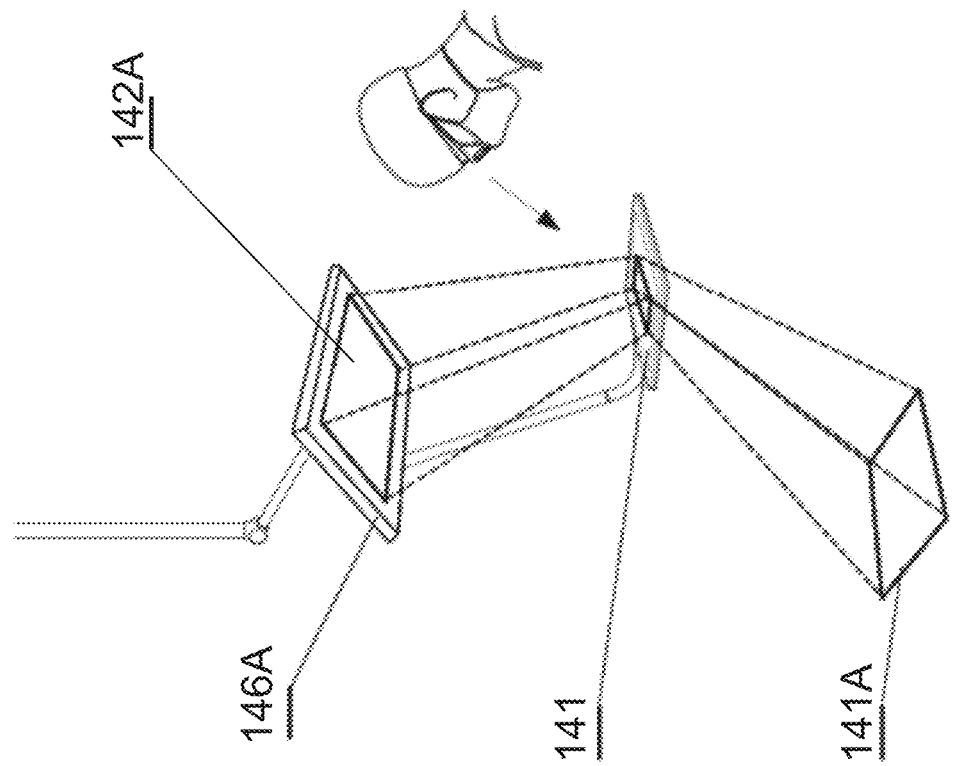
FIG. 4C shows another embodiment of a 3D display system for use in an embodiment of the invention.
Figure 4B:
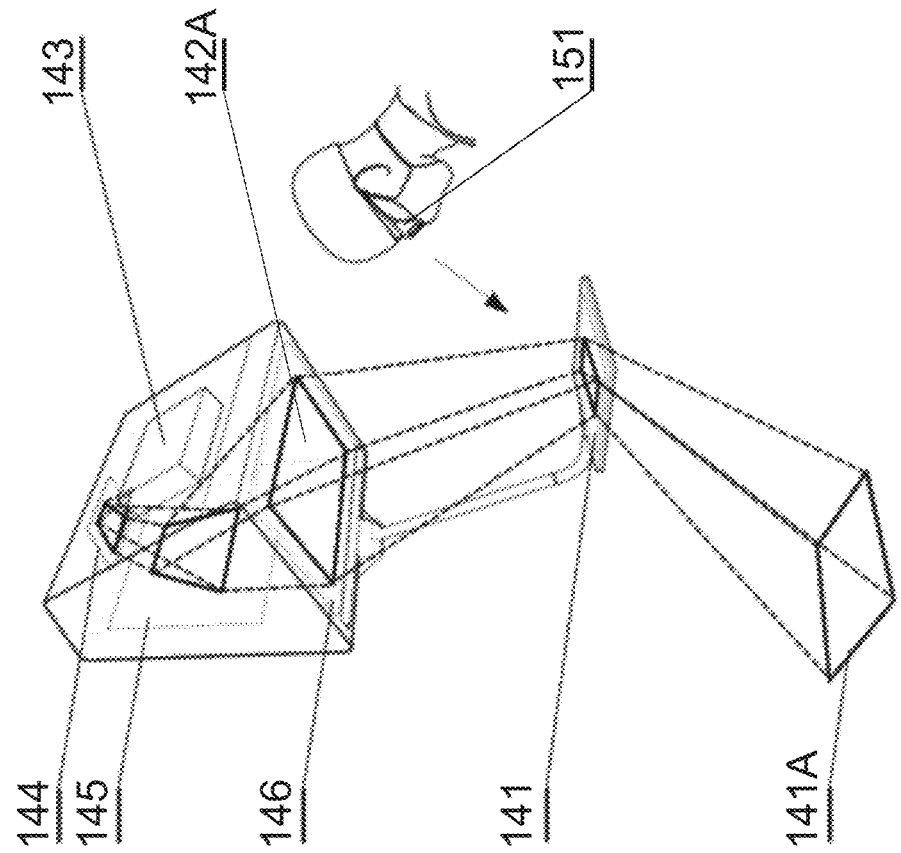
FIG. 4B shows another embodiment of a 3D display system for use in an embodiment of the invention.

In an example embodiment as shown in FIGS. 4A and 4B, a special design of the 3D display 142 is provided that is compact in size to facilitate its mounting within a limited space at the operating room. That design allows generating images of relatively large size, taking into account the small distance between the 3D display 142 and the see-through mirror 141, without the need to use wide-angle lens that could distort the image.

The 3D display 142 comprises a 3D projector 143, such as a DLP projector, that is configured to generate an image, as shown in FIG. 4B (by the dashed lines showing image projection and solid lines showing images generated on particular reflective planes). The image from the 3D projector 143 is firstly refracted by an opaque top mirror 144, then it is refracted by an opaque vertical mirror 145 and subsequently placed on the correct dimensions on a projection screen 146 (which can be simply a glass panel). The projection screen 146 works as a rear-projection screen or a small bright 3D display. The image displayed at the projection screen 146 is reflected by the see-through mirror 141 which works as an augmented reality device. Such configuration of the mirrors 144, 145 allows the image generated by the 3D projector 143 to be shown with an appropriate size at the projection screen 146. The fact that the projection screen 146 emits an enlarged image generated by the 3D projector 143 makes the emitted surgical navigation image bright, and therefore well visible when reflected at the see-through mirror 141. Reference 141A indicates the augmented reality image as perceived by the surgeon when looking at the see-through mirror 141.

The see-through mirror 141 is held at a predefined position with respect to the 3D projector 143, in particular with respect to the 3D projector 143, by an arm 147, which may have a first portion 147A fixed to the casing of the 3D display 142 and a second portion 147B detachably fixed to the first portion 147A. The first portion 147A may have a protective sleeve overlaid on it. The second portion 147B, together with the see-through mirror 141, may be disposable in order to maintain the sterility of the operating room, as it is relatively close to the operating field and may be contaminated during the operation. The arm can also be foldable upwards to leave free space of the work space when the arm and augmented reality are not needed.

Figure 4E:
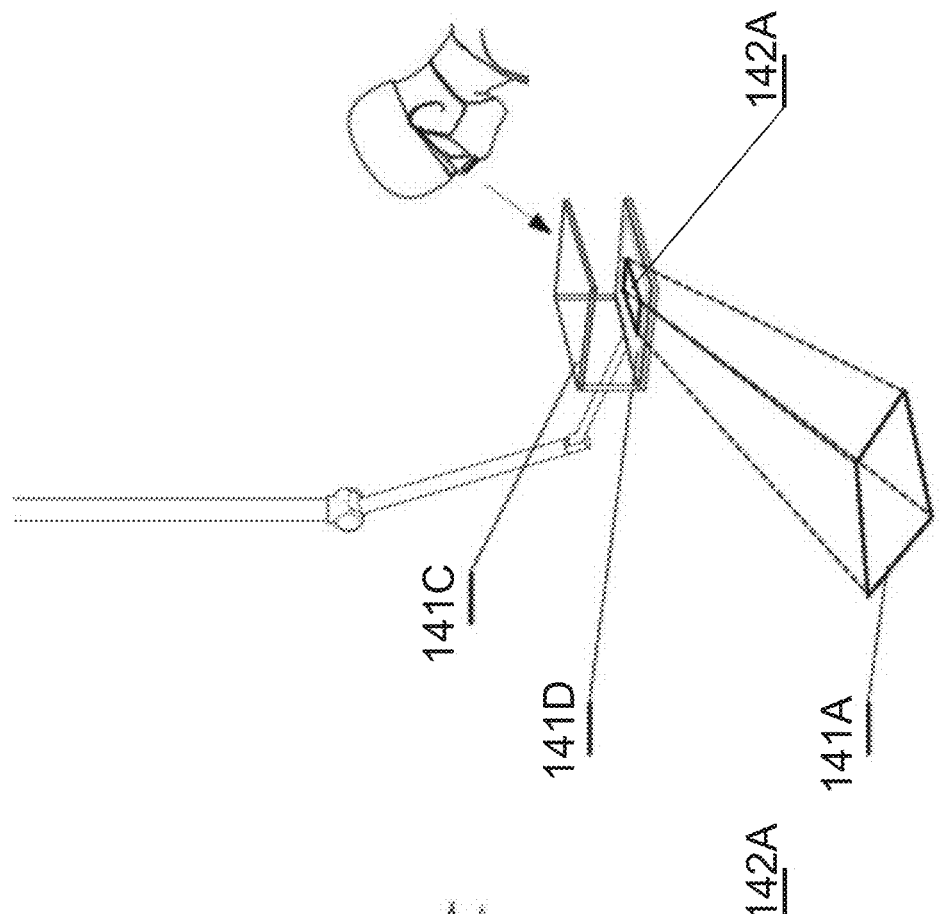
FIG. 4E shows another embodiment of a 3D display system for use in an embodiment of the invention.
Figure 4D:
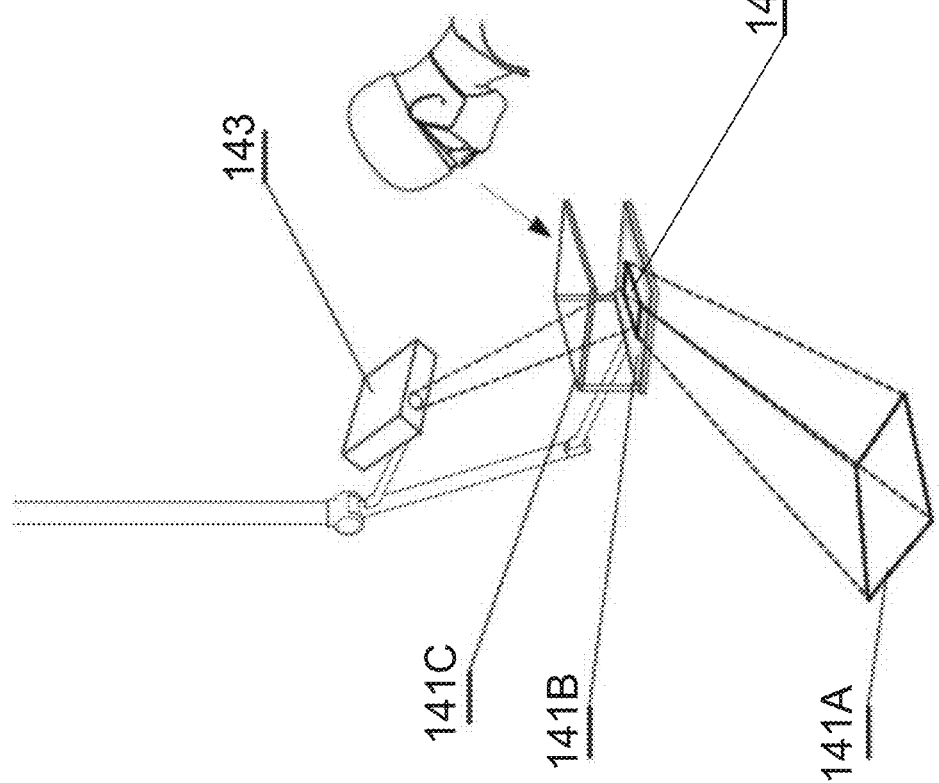
FIG. 4D shows another embodiment of a 3D display system for use in an embodiment of the invention.

In alternative embodiments, as shown for example in FIGS. 4C, 4D, 4E, alternative devices may be used in the 3D display system 140 in place of the see-through mirror 141 and the 3D display 142.

As shown in FIG. 4C, a 3D monitor 146A can be used directly in place of the projection screen 146.

As shown in FIG. 4D, a 3D projector 143 can be used instead of the 3D display 142 of FIG. 4A, to project the surgical navigation image onto a see-through projection screen 141B, which is partially transparent and partially reflective, for showing the surgical navigation image 142A and allowing the surgical field 108 to be seen. A lens 141C can be used to provide appropriate focal position of the surgical navigation image.

As shown in FIG. 4E, the surgical navigation image can be displayed at a three-dimensional see-through display 141D and viewed by the user via a lens 141C used to provide appropriate focal position of the surgical navigation image.

Therefore, each of the see-through projection screen 141B, the see-through display 141D and the see-through mirror 141 can be commonly called a see-through device.

If a need arises to adapt the position of the augmented reality screen with respect to the surgeon's head (for example, to accommodate the position depending on the height of the particular surgeon), the position of the whole 3D display system 140 can be changed, for example by manipulating an adjustable holder (a surgical boom) 149 on FIG. 1A, by which the 3D display 142 is attachable to an operating room structure, such as a ceiling, a wall or a floor.

An eye tracker 148 module can be installed at the casing of the 3D display 142 or at the see-through device 141 or at the wearable glasses 151, to track the position and orientation of the eyes of the surgeon and input that as commands via the gaze input interface to control the display parameters at the surgical navigation image generator 131, for example to activate different functions based on the location that is being looked at, as shown in FIGS. 5A and 5B.

For example, the eye tracker 148 may use infrared light to illuminate the eyes of the user without affecting the visibility of the user, wherein the reflection and refraction of the patterns on the eyes are utilized to determine the gaze vector (i.e. the direction at which the eye is pointing out). The gaze vector along with the position and orientation of the user's head is used to interact with the graphical user interface. However, other eye tracking algorithms techniques can be used as well.

It is particularly useful to use the eye tracker 148 along with the pedals 132 as the input interface, wherein the surgeon may navigate the system by moving a cursor by eyesight and inputting commands (such as select or cancel) by pedals.

While the invention has been described with respect to a limited number of embodiments, it will be appreciated that many variations, modifications and other applications of the invention may be made. Therefore, the claimed invention as recited in the claims that follow is not limited to the embodiments described herein.

What is claimed is:

1. A surgical navigation system, comprising:
    a three-dimensional (3D) display system;
    a tracker configured to track a position and orientation of a robot arm, a head of a surgeon, the 3D display system, a surgical instrument, and a patient anatomy in a surgical field to provide current position and orientation data of the robot arm, the head of the surgeon, the 3D display system, the surgical instrument, and the patient anatomy;
    a source of a patient anatomical data, a surgical instrument model, and a robot arm data; and
    a surgical navigation image generator configured to generate a surgical navigation image comprising a virtual representation of at least a portion of the patient anatomy, a virtual representation of at least a portion of the surgical instrument, and a virtual representation of at least a portion of the robot arm based on the current position and orientation data provided by the tracker and using the patient anatomical data, the surgical instrument model, and the robot arm data;
    the 3D display system configured to display the surgical navigation image to the surgeon such that the virtual representation of the portion of the patient anatomy is collocated with the patient anatomy in the surgical field, the virtual representation of the portion of the surgical instrument is collocated with the surgical instrument, and the virtual representation of the portion of the robot arm is collocated with the robot arm.

2. The system of claim 1, wherein the 3D display system is configured to selectively show or hide the display of the virtual representation of the portion of the robot arm.

3. The system of claim 1, wherein the 3D display system is configured to adjust an opacity of the display of the virtual representation of the portion of the robot arm.

4. The system of claim 1, wherein:
    the patient anatomical data comprises a 3D reconstruction of a segmented model of the patient anatomy comprising at least two sections representing parts of the patient anatomy; and
    the 3D display system is configured to adjust the display of the portion of the patient anatomy such that at least one section of the patient anatomy is displayed while at least one other section of the patient anatomy is not displayed.

5. The system of claim 1, further comprising:
    a source of an operative plan;
    wherein the surgical navigation image further comprises surgical guidance indicating at least one of a trajectory or a placement of the surgical instrument according to the operative plan.

6. The system of claim 5, wherein the surgical guidance indicates a suggested position and orientation of the surgical instrument according to the operative plan.

7. The system of claim 6, wherein the surgical guidance includes a graphical cue indicating a required change of a current position and orientation of the surgical instrument to match the suggested position and orientation according to the operative plan.

8. The system of claim 1, wherein the surgical navigation image further comprises a set of orthogonal or arbitrary planes of the patient anatomy.

9. The system of claim 1, wherein the 3D display system is configured to display the surgical navigation image at a see-through device, and wherein the tracker is configured to track a position and orientation of the see-through device such that the surgical navigation image being displayed at the see-through device has the virtual representation of the portion of the patient anatomy collocated with the patient anatomy in the surgical field, the virtual representation of the portion of the surgical instrument collocated with the surgical instrument, and the virtual representation of the portion of the robot arm collocated with the robot arm underneath the see-through device when viewed by the surgeon looking from above the see-through device towards the surgical field.

10. The system of claim 1, wherein the patient anatomical data comprises output data of a semantic segmentation process of a set of two-dimensional (2D) images of the patient anatomy.

11. The system of claim 1, further comprising a convolutional neural network system configured to perform the semantic segmentation process to generate the patient anatomical data.

12. A method for providing an augmented reality image during an operation, comprising:
    obtaining a source of a patient anatomical data, a surgical instrument model, and a robot arm data;
    tracking a position and orientation of a robot arm, a head of a surgeon, a three-dimensional (3D) display system, and a patient anatomy in a surgical field to provide current position and orientation data of the robot arm, the head of the surgeon, the 3D display system, the surgical instrument, and the patient anatomy;
    generating, by a surgical navigation image generator, a surgical navigation image comprising a virtual representation of at least a portion of the patient anatomy, a virtual representation of at least a portion of the surgical instrument, and a virtual representation of at least a portion of the robot arm based on the current position and orientation data provided by the tracker and using the patient anatomical data, the surgical instrument model, and the robot arm data; and
    displaying the surgical navigation image at a 3D display system such that the virtual representation of the portion of the patient anatomy is collocated with the patient anatomy in the surgical field, the virtual representation of the portion of the surgical instrument is collocated with the surgical instrument, and the virtual representation of the portion of the robot arm is collocated with the robot arm.

13. The method of claim 12, further comprising selectively showing or hiding at the 3D display system the display of the virtual representation of the portion of the robot arm.

14. The method of claim 12, further comprising adjusting at the 3D display system an opacity of the display of the virtual representation of the portion of the robot arm.

15. The method of claim 12, wherein the patient anatomical data comprises a 3D reconstruction of a segmented model of the patient anatomy comprising at least two sections representing parts of the patient anatomy, the method further comprising:

adjusting at the 3D display system the display of the portion of the patient anatomy such that at least one section of the patient anatomy is displayed while at least one other section of the patient anatomy is not displayed.

16. The method of claim 12, further comprising obtaining a source of an operative plan,
wherein the surgical navigation image further comprises surgical guidance indicating at least one of a trajectory or a placement of the surgical instrument according to the operative plan.

17. The method of claim 16, wherein the surgical guidance indicates a suggested position and orientation of the surgical instrument according to the operative plan.

18. The method of claim 17, wherein the surgical guidance includes a graphical cue indicating a required change of a current position and orientation of the surgical instrument to match the suggested position and orientation according to the operative plan.

19. The method of claim 17, wherein the surgical navigation image further comprises a set of orthogonal or arbitrary planes of the patient anatomy.

20. The method of claim 12, wherein the position and the orientation of the robot arm is tracked by a tracker that tracks a marker array attached to a portion of the robot arm and by encoders positioned at one or more joints of the robot arm.

* * * * *